(12) United States Patent
Shah et al.

(10) Patent No.: US 11,996,171 B2
(45) Date of Patent: May 28, 2024

(54) SYSTEM AND METHOD FOR PROVIDING AGGREGATION AND CONTINUOUS LEARNING TO IMPROVE HEALTH OUTCOMES (71) Applicant: Samsung Electronics Co., Ltd., Suwon-si (KR)

(72) Inventors: Divya Shah, Sunnyvale, CA (US); Alireza Aliamiri, San jose, CA (US); Euan S. Thomson, Los Gatos, CA (US); Tejash Prakash Shah, San Mateo, CA (US)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 1251 days.

(21) Appl. No.: 15/497,165

(22) Filed: Apr. 25, 2017

(65) Prior Publication Data

US 2017/0308666 A1 Oct. 26, 2017

Related U.S. Application Data (60) Provisional application No. 62/327,403, filed on Apr. 25, 2016.

(51) Int. Cl.
H04L 67/10 (2022.01)
G06N 3/006 (2023.01)
(Continued)

(52) U.S. Cl.
CPC .............. *G16H 10/60* (2018.01); *G06N 3/006* (2013.01); *G06N 3/08* (2013.01); *G06N 20/00* (2019.01);
(Continued)

(58) Field of Classification Search
CPC ........ G16H 20/60; G16H 20/30; G16H 40/67; G16H 10/60; G16H 50/20; G16H 15/00;
(Continued)

(56) References Cited

U.S. PATENT DOCUMENTS 8,866,606 B1 * 10/2014 Will ..................... G08B 25/005
455/418
2013/0158367 A1 6/2013 Pacione et al.
(Continued)

FOREIGN PATENT DOCUMENTS

CN 104834827 8/2015
KR 20130065755 A 6/2013
(Continued)

OTHER PUBLICATIONS

Int'l Search Report and Written Opinion for Appln. No. PCT/IB2017/000645 dated Aug. 30, 2017.
(Continued)

*Primary Examiner* — Reginald R Reyes
(74) *Attorney, Agent, or Firm* — McAndrews, Held & Malloy, Ltd.

(57) ABSTRACT

Provided is a method and system for helping a user reach a health goal. Various embodiments of the disclosure disclose receiving various data that relate to the user and comparing the received data to monitored user health data to provide recommendations on steps to take to achieve the health goal. The various embodiments also determine when the user has achieved the user's desired health goal.

16 Claims, 9 Drawing Sheets (51) Int. Cl.
*G06N 3/08* (2023.01)
*G06N 20/00* (2019.01)
*G16H 10/60* (2018.01)
*G16H 40/67* (2018.01)
*G06Q 10/109* (2023.01)
*G16H 20/30* (2018.01)
*G16H 20/60* (2018.01)
*G16H 20/70* (2018.01)

(52) U.S. Cl.
CPC ............. *G16H 40/67* (2018.01); *H04L 67/10* (2013.01); *G06Q 10/109* (2013.01); *G16H 20/30* (2018.01); *G16H 20/60* (2018.01); *G16H 20/70* (2018.01)

(58) Field of Classification Search
CPC ........ G16H 20/10; G16H 20/70; G16H 50/70; G16H 70/40; G16H 20/17; G16H 40/63; G16H 50/30; G16H 70/20; G16H 80/00
See application file for complete search history.

(56) References Cited

U.S. PATENT DOCUMENTS

| | | | |
|---|---|---|---|
| 2014/0347491 A1 | 11/2014 | Connor | |
| 2015/0269848 A1 | 9/2015 | Yuen et al. | |
| 2015/0294574 A1 | 10/2015 | Pacione et al. | |
| 2015/0294575 A1 | 10/2015 | Pacione et al. | |
| 2016/0012197 A1* | 1/2016 | Eromo | G16H 50/20 705/2 |
| 2016/0119293 A1* | 4/2016 | Leon | H04L 9/321 713/168 |
| 2016/0140870 A1* | 5/2016 | Connor | G01J 3/0256 356/51 |
| 2017/0116497 A1* | 4/2017 | Georgescu | G06N 3/006 |
| 2017/0220751 A1* | 8/2017 | Davis | G06N 5/048 |
| 2017/0308666 A1* | 10/2017 | Thomson | H04L 67/10 |

FOREIGN PATENT DOCUMENTS

| | | |
|---|---|---|
| WO | 2015051055 | 4/2015 |
| WO | 2015089484 | 6/2015 |

OTHER PUBLICATIONS

Int'l Preliminary Report on Patentability for Appln. No. PCT/IB2017/000645 dated Nov. 8, 2018.

* cited by examiner

SYSTEM AND METHOD FOR PROVIDING AGGREGATION AND CONTINUOUS LEARNING TO IMPROVE HEALTH OUTCOMES

RELATED APPLICATION(S)

This application claims the benefit of priority to the U.S. Provisional Application 62/327,403, filed on Apr. 25, 2016, the disclosure of which is incorporated herein in its entirety by reference.

BACKGROUND

A number of electronic device (e.g., a mobile phone, a tablet) applications and websites typically provide tracking of diet and exercise of a user to determine optimal caloric intake and nutrients for the user's health goal. Such applications and websites require a user to rigorously provide his/her food intake and activity descriptions in order to monitor the user's information.

SUMMARY

Various aspects of this disclosure provide systems and methods for aggregating and continuous learning to improve health outcomes. As non-limiting examples, various aspects of this disclosure provide various methods of collecting biometric data of a person as well as context data of the person and the environment in which the person is present at various times of the day.

Additional aspects will be set forth in the description that follows and/or learned by practice of the presented by various example embodiments.

BRIEF DESCRIPTION OF THE DRAWINGS

These aspects of the disclosure will become apparent and more readily appreciated when taken in conjunction with the accompanying drawings.

DETAILED DESCRIPTION

As utilized herein, "and/or" means any one or more of the items in the list joined by "and/or." As an example, "x and/or y" means any element of the three-element set {(x), (y), (x, y)}. In other words, "x and/or y" means "one or both of x and y." As another example, "x, y, and/or z" means any element of the seven-element set {(x), (y), (z), (x, y), (x, z), (y, z), (x, y, z)}. In other words, "x, y and/or z" means "one or more of x, y and z". As utilized herein, the term "exemplary" means serving as a non-limiting example, instance, or illustration. As utilized herein, the terms "e.g." and "for example" set off lists of one or more non-limiting examples, instances, or illustrations.

Also, the singular forms are intended to include the plural forms as well, unless the context clearly indicates otherwise. It will be further understood that the terms "comprises," "comprising," "includes," and/or "including," when used in this specification, specify the presence of stated features, numbers, steps, operations, elements, and/or components, but do not preclude the presence or addition of one or more other features, numbers, steps, operations, elements, components, and/or groups thereof.

In addition, it will be understood that when an element A is referred to as being "connected to" or "coupled to" an element B, the element A can be directly connected to or coupled to the element B, or an intervening element C may be present between the elements A and B so that the element A can be indirectly connected to or coupled to the element B.

Furthermore, although the terms first, second, etc. may be used to describe various members, elements, regions, layers and/or sections, these members, elements, regions, layers and/or sections should not be limited by these terms. These terms are only used to distinguish one member, element, region, layer, and/or section from another. Thus, for example, a first member, a first element, a first region, a first layer, and/or a first section discussed below could be termed a second member, a second element, a second region, a second layer, and/or a second section without departing from the teachings of the present disclosure.

Spatially relative terms, such as "upper," "lower," "side," and the like, may be used for ease of description to describe the relationship of one element or feature to another element(s) or feature(s) as illustrated in the figures. It will be understood that the spatially relative terms are intended to encompass different orientations of the device in use or operation in addition to the orientation depicted in the figures. For example, if the device in the figures is turned upside-down, elements described as "below" or "beneath" other elements or features would then be oriented "above" the other elements or features. Thus, for example, the term "below" can encompass both an orientation of above and below.

The term "unit" in the embodiments of the present disclosure means a software component or a hardware component that performs a specific function. A hardware component may include, for example, a field-programmable gate array (FPGA) or an application-specific integrated circuit (ASIC). A software component may refer to executable code and/or data used by the executable code in an addressable storage medium. Thus, software components may be, for example, object-oriented software components, class components, and task components, and may include processes, functions, attributes, procedures, subroutines, segments of program code, drivers, firmware, micro codes, circuits, data, a database, data structures, tables, arrays, or variables.

A function provided by a "unit" may be divided into additional components and "units."

Advantages and features of one or more embodiments of the present disclosure may be understood more readily by reference to the following detailed description of the embodiments and the accompanying drawings.

In this regard, the present embodiments should not be construed as being limited to the descriptions set forth herein. Rather, these embodiments are provided as examples so that this disclosure will be thorough and complete and will fully convey the concept of the present embodiments to one of ordinary skill in the art. The appended claims illustrate some of the embodiments of the present disclosure.

The terminology used here is for the purpose of describing particular embodiments only and is not intended to limit the disclosure. All terms including descriptive or technical terms used herein should be construed as having meanings that are obvious to one of ordinary skill in the art. When a term has an ambiguous meaning due to evolving of language, precedent cases, and/or the appearance of new technologies, the meaning of a term used in this disclosure should first be clarified by its usage and/or definition in this disclosure. If further clarification is needed, the term should then be clarified as one of ordinary skill in the art would have understood the term in context of the disclosure at the time of the disclosure.

In the drawings, the thickness of layers and regions may be exaggerated for clarity. Like reference numerals refer to like elements throughout.

An embodiment of the disclosure provides for a method for monitoring health of a user comprising receiving user-related data from at least one electronic device, and monitoring health related data of the user. Then a correlation may be determined between the user-related data and the health related data, and at least one recommendation may be made based on the correlation.

Another embodiment of the disclosure provides for a system comprising an input/output device configured to receive user-related data from at least one electronic device, and receive monitored health related data of the user. The system may also comprise a processor configured to determine a correlation between the user-related data and the health related data, and provide at least one recommendation to the user based on the correlation.

Still another embodiment of the disclosure provides for a non-transitory machine-readable medium storing machine executable instructions that when executed causes a computing system to control operations comprising monitoring health of a user, wherein an input-output (TO) device is configured to receive user-related data from at least one electronic device, and monitor health related data of the user. The machine executed instructions may also cause the computing system to control operations wherein a processor is configured to determine a correlation between the user-related data and the health related data, and provide at least one recommendation to the user based on the correlation.

Reference will now be made in detail to various embodiments, examples of which are illustrated in the accompanying drawings. In this regard, the present embodiments may have different forms and should not be construed as being limited to the descriptions set forth herein.

In the following description, well-known functions or constructions may not be described in detail so as not to obscure the embodiments with unnecessary detail.

Various embodiments of the disclosure may provide a cross platform interoperability solution for receiving multiple types of data to provide deep learning health and behavior modification insights to a user (e.g., a patient, a clinician) aimed at improving health outcomes of a person (or patient).

For example, an application with a user interface may allow a user to configure a personalized and customized profile to curate one or more desired goals based on monitored health measurement data. For example, the desired goal may be a desired medical trend such as, for example, blood pressure control, blood glucose level control, etc. The desired goal may also be fitness-related such as, for example, desired weight loss, muscle gain, strength improvement, desired athletic performance, etc. The desired goal may be, for example, lifestyle-related to lead a less stressful lifestyle, a happier work life, etc. Accordingly, an embodiment may monitor the health measurement data (or health related data) with the corresponding one or more of lifestyle data, clinical data, context data, environmental data, and food consumption data, and provide a health profile recommendation to help the user achieve the desired goal. An embodiment may also provide a health profile recommendation that is personalized for each user including information from one or more of health measurement data, lifestyle data, food consumption data, context data, and clinical data, and recommendations for an adjustment in one or more of nutrition, lifestyle, and fitness activities to achieve a desired goal.

It should be realized that there may be overlap in the various data received from the various sources. For example, the monitored health related data of the user may include weight measured with a smart weighing scale that may communicate the user's weight to another device, or store the information for later transmission. The user's weight may also be downloaded as part of clinical data from, for example, a doctor's office.

Figure 1:
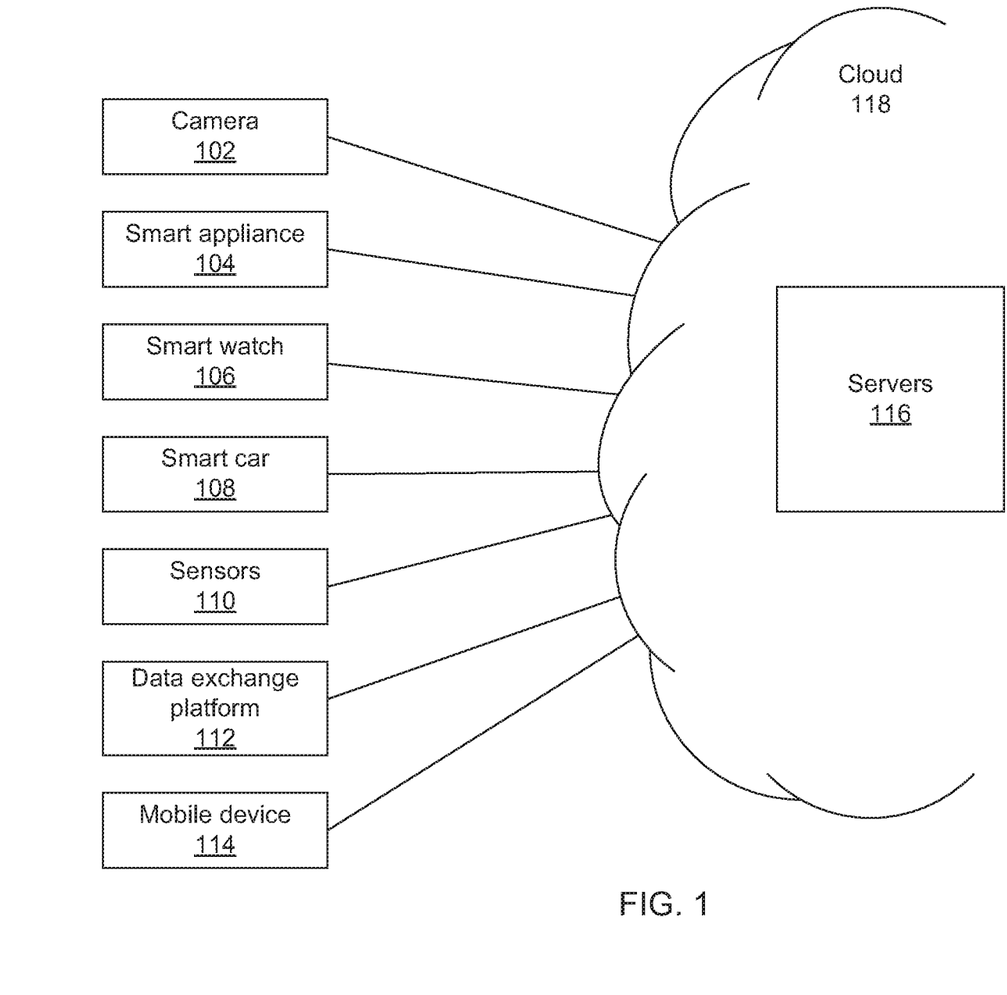
FIG. 1 is a diagram illustrating data sent to the cloud by electronic devices in accordance with an embodiment of the present disclosure.

FIG. 1 is a diagram illustrating an overview of a network environment in accordance with an embodiment of the present disclosure. Referring to FIG. 1, there are shown various devices that can provide input for aggregation and continuous learning to improve health outcomes. These devices are representative and should not be construed as being the entirety of a set of data providing devices.

The examples of devices that can provide data are cameras 102, smart appliances 104 (for example, a smart refrigerator), smart watches 106, smart cars 108, sensors 110, data exchange platforms 112, and various mobile devices 114 (for example, mobile phones). These devices and sensors may provide information about the user's activities, food intake, environmental data that may cause stress to the user, etc. All this data may be sent to one or more servers 116 in the cloud 118 where the server(s) may process the data for the benefit of the user. The data may be sent to the cloud 118 by a device, or data from a device may be sent to the cloud via another device. The process for using the data will be described later.

While an embodiment may use server(s) 116 in the cloud 118 for receiving and processing data, various embodiments of the disclosure may use one or more personal devices, such as, for example, the smart watch 106, the mobile device 114, a personal computer (not shown), etc. for receiving and/or processing data. The mobile device 114 may include, for example, a smartphone, a tablet, a laptop, etc.

The camera 102, which may be a part of various devices or a stand-alone camera, may provide pictures and/or video to indicate the environment that the user is in. This may help indicate, for example, whether the user is resting in a peaceful setting.

The smart appliance 104, such as, for example, a smart refrigerator, may provide information about the types of food and quantity in the refrigerator over time, thus allowing an inference of the diet of the user.

The smart watch 106 may provide various biometric data for the user. For example, the biometric data may include the user's pulse rate and body temperature among other data. Accordingly, various biometric sensors available with present technology may be used. As technology progresses, other biometric sensors may be used.

The smart car 108 may provide data regarding the user's environment while driving such as, for example, traffic, pollen count, air pollution data, etc. The data may indicate an amount of stress/discomfort that the user may have. The position of the smart car 108 may also allow suggestions, for example, of places to eat in accordance with a diet that may be recommended for the user.

The sensors 110 may include sensors in other devices and/or stand-alone sensors. The stand-alone sensors may be, for example, various medical equipments at a doctor's office or clinic/hospital for providing more accurate health information than may be possible with sensors in user devices.

The data exchange platform 112 may be used to receive data that can be used by the server(s) 116 to, for example, receive data for other people with similar profiles as the user to allow an initial population of data for the user. The data may be refined for the user as more user data is gathered over time.

The mobile device 114 may be used to gather various user data using built-in sensors or other sensors, and/or display output to the user. The output may be, for example, a recommendation or guidance on diet, exercise, the user's progress toward a desired goal, etc.

Figure 2A:
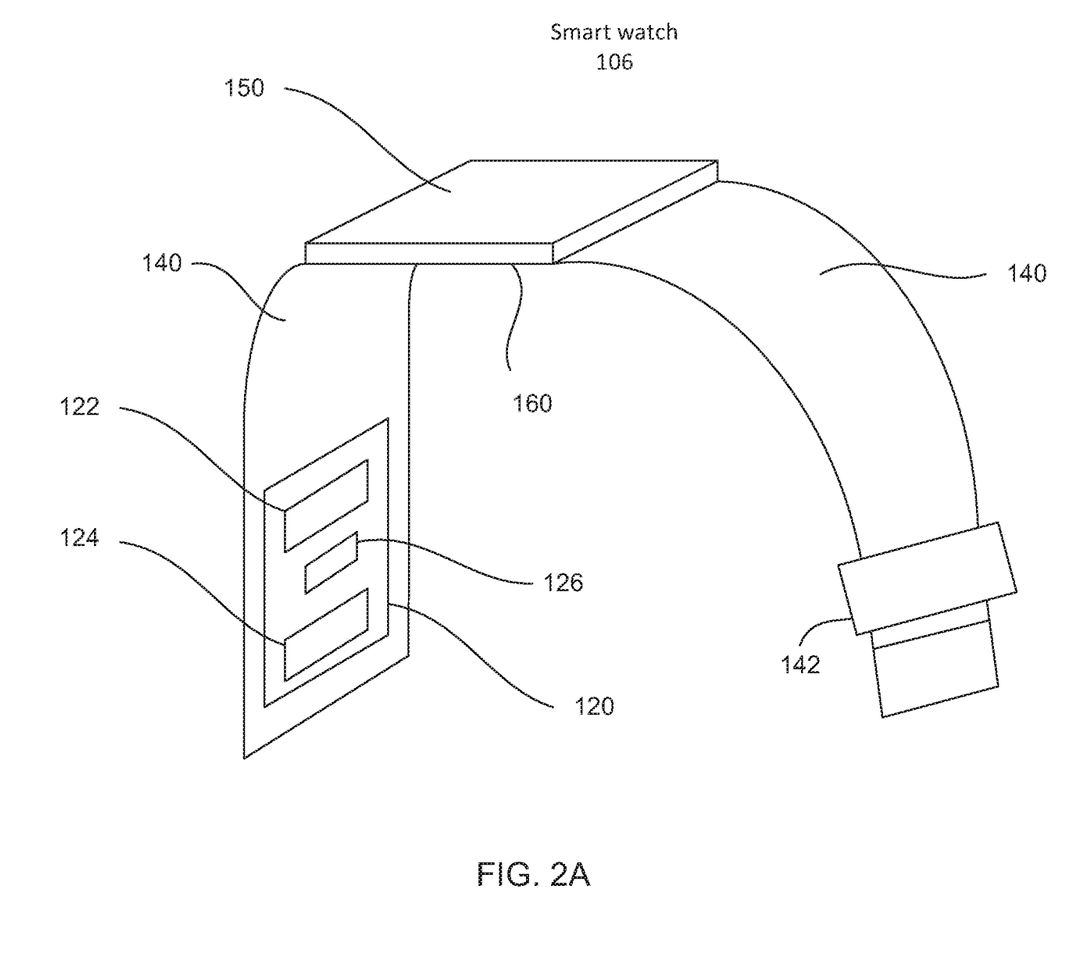
FIG. 2A is a diagram of a wearable electronic device that can be used with an embodiment of the present disclosure.

FIG. 2A is a diagram illustrating an electronic device in accordance with an embodiment of the present disclosure. Referring to FIG. 2A, there is shown an electronic device, which may be the smart watch 106 with a display 150, processors 126 and 160, and a strap 140 with a clasp 142 and a sensor module 120. The sensor module 120 may include processor 126 and sensors 122 and 124.

Although the smart watch 106 may be worn on a wrist, various embodiments of the disclosure need not be so limited. The smart watch 106 or other wearable electronic devices may also be designed to be worn on other parts of the body, such as, for example, on an arm (around the forearm, the elbow, or the upper arm), on a leg, around the chest, around the head like a headband, around the throat like a "choker," and on an ear. The smart watch 106 may be able to communicate with other electronic devices such as, for example, a laptop, to various electronic devices including those described in FIG. 1, the server(s) 116, etc. This will be described in more detail with respect to FIG. 3.

The smart watch 106 may monitor a user's physiological signals via the sensor module 120, as well as receive data from other devices/servers via an input/output (IO) interface 220 and/or a communication interface 230 (to be described later with respect to FIG. 2B). The signals monitored by the sensor module 120 may be referred to as biosignals or biometric data. The monitored signals may be, for example, pulse rate, pulse morphology (shape), and/or pulse spacing (inter-beat intervals). The user-wearable device 100 may also, for example, receive continuous glucose reading from an under-skin sensor (not shown) placed under the user's skin. While the present technology may place the continuous glucose monitoring sensor under the user's skin, if a future technology allows a glucose monitoring sensor that does not need to be placed under the user's skin, that sensor may be integrated as a part of the smart watch 106 or other appropriate device.

The display 150 may output instructions to the user or others in the use of the smart watch 106, status and diagnostic results, as well as display various charts, health profile recommendations(s) for achieving desired health goals, the trend in the process of reaching the goal, etc. Some of these health goals may be, for example, controlling blood glucose level trend, losing weight, sleeping better, increasing strength, etc.

The processor 160 may process the monitored signals to determine whether a more detailed monitoring and/or a different type of monitoring may be needed. The processor 160 may also process various data received by the smart watch 106 from the various electronic devices described in FIG. 1, or the processor 160 may be used in conjunction with the server(s) 116 and/or other processing devices.

The sensor module 120 may include, for example, sensors 122 and 124 that either touch the user's wrist or is in close proximity to the user's wrist when the smart watch 106 is worn by the user. The processor 126 may control the sensors 122 and 124, and may also process the signals monitored by the sensors 122 and 124. For example, the processor 126 may filter noise from the signals monitored by the sensors 122 and 124. Various embodiments of the disclosure may have the processor 160 also perform the functions of the processor 126, or the processor 126 may be used in conjunction with the processor 160 for various tasks such as, for example, processing data received from other electronic devices.

The sensor 122 may be, for example, a sensor that is used to continuously or near continuously monitor pulse related information. The sensor 124 may be, for example, an ECG sensor. The sensor 122 or 124 may be any appropriate sensor for monitoring biometric data of the user. Various embodiments of the disclosure may also have different number of sensors.

The smart watch 106 may provide continuous monitoring or periodic monitoring. The specific type of monitoring may be design and/or implementation dependent, and may also include an option that allows the user to select the type of monitoring. Periodic monitoring may alternate monitoring period and a non-monitoring period. Periodic monitoring may be to allow for longer battery life.

While the smart watch 106 was described as an example of an electronic device, other electronic devices may also be used that are not smart watches.

Figure 2B:
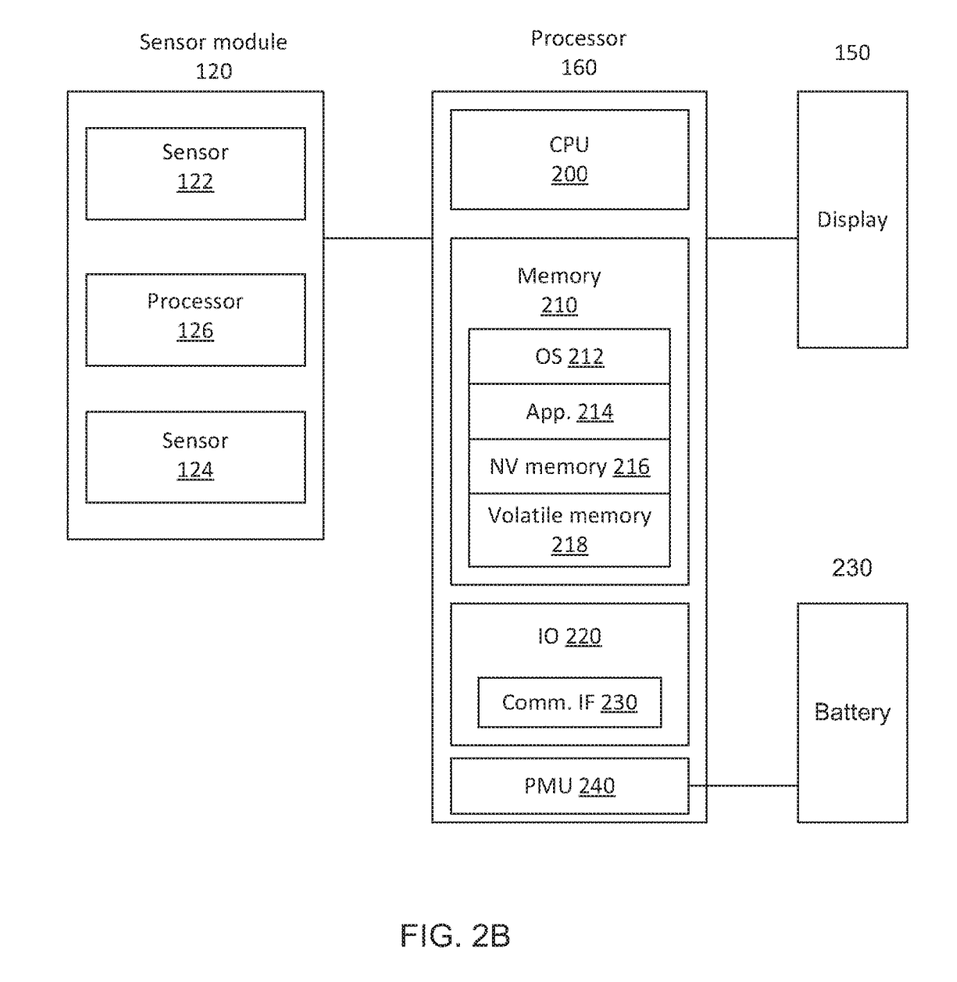
FIG. 2B is a block diagram of a user electronic device that can be used with an embodiment of the present disclosure.

FIG. 2B is a high-level block diagram of an electronic device in accordance with an embodiment of the present disclosure. Referring to FIG. 2, there is shown the display 150, the processor 160, the sensor module 120, and the battery 250. Output to the display 150 may be controlled by the processor 160. The display 150 may also include input devices (not shown) such as, for example, buttons, dials, touch sensitive screen, and microphone.

The processor 160 may include a CPU 200, memory 210, an input/output (TO) interface 220, a communication interface 230, and a power management unit (PMU) 240. While the processor 160 is described as comprising these various devices, other embodiments may use other architectures where the different functionalities are grouped differently. For example, the grouping may be in different integrated circuit chips. Or the grouping may separate devices such as the IO interface 220 and the communication interface 230.

The CPU 200 may control operation of the sensor module 120 as well as receive monitored signals from the sensor module 120. The CPU 200 may control the electronic device, which may be the smart watch 106, including processing the monitored signals from the sensor module 120 as well as other data received from other sources, displaying the processed signals/data on the display 150, receiving input from the display 150, interfacing with various devices via the IO interface 220 and/or the communication interface 230 by executing instructions in the memory 210. The IO interface 220 may be used, for example, by the CPU 200 to interface with the display 150.

The processor 126 may operate using different architectures in different embodiments. For example, the processor 126 may use the memory 210 to store instructions to execute, or the processor 126 may have its own memory (not shown) for its instructions. Although some embodiments have separate processors 126 and 160, the various embodiments need not be limited so. There may be one processor 160 that controls the functionality of the electronic device, or there may be multiple processors for the electronic device.

The memory 210 may include non-volatile memory 216 and volatile memory 218. The operating system and applications may be stored in the non-volatile memory 216. Various embodiments of the disclosure may use different memory architectures that are design and or implementation dependent.

The communication interface 230 may allow the user-wearable device 100 to communicate with other devices via, for example, a wired protocol such as USB or a wireless protocol such as Bluetooth, Near Field Communication (NFC), and WiFi. The PMU 240 may control receiving power from an outside source, charging the battery 250 if there is a battery 250, as well as allocation of power to the different parts of the electronic device.

Figure 3:
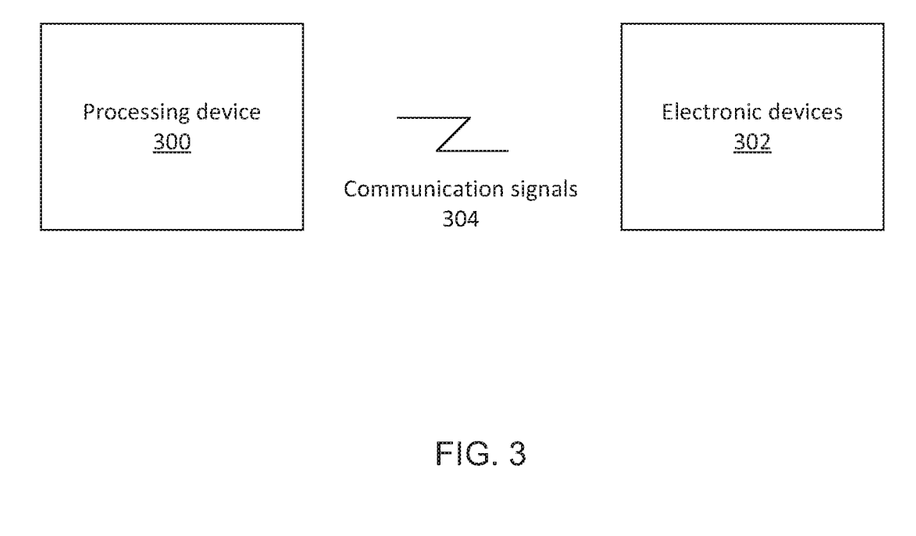
FIG. 3 is an illustration of user device communicating with other devices in accordance with an embodiment of the present disclosure.

FIG. 3 is an illustration of an electronic device in a communication network in accordance with an embodiment of the present disclosure. Referring to FIG. 3, there is shown a processing device 300 and electronic device(s) 302. The processing device 300 may be, for example, the server(s) 116, the smart watch 106, or other appropriate electronic device(s) that can be used in various embodiments of the disclosure. The processing device 300 may communicate with the electronic device(s) 302 using the communication interface 230. The communication may be via communication signals 304 between the processing device 300 and the electronic device(s) 302. The communication signals 304 may be via a wired communication protocol or a wireless communication protocol. Although not shown, the communication signals 304 may be sent via one or more communication units between the processing device 300 and the electronic device(s) 302. For example, the processing device 300 and the electronic device(s) 302 may belong to the same network or different networks.

Figure 4:
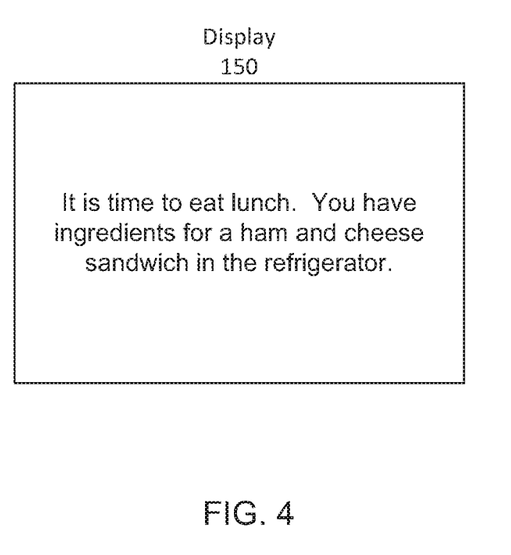
FIG. 4 is an example of a notification to the user in accordance with an embodiment of the present disclosure.

FIG. 4 is an example of a notification to the user in accordance with an embodiment of the present disclosure. Referring to FIG. 4, various instructions, status, or recommendation/guidance may be shown on the display 150. The output may indicate, for example, nearby places to eat in accordance with a diet for the user, the available groceries in the smart refrigerator (smart appliance 104), the next exercise to be done, etc. The output may also be, for example, a display of the progress toward the desired goal, a number of steps taken, other exercises performed, biometric data, etc.

Various embodiments of the disclosure may provide output at different display device(s) that may be a stand-alone display or a display built in to an electronic device.

Figure 5:
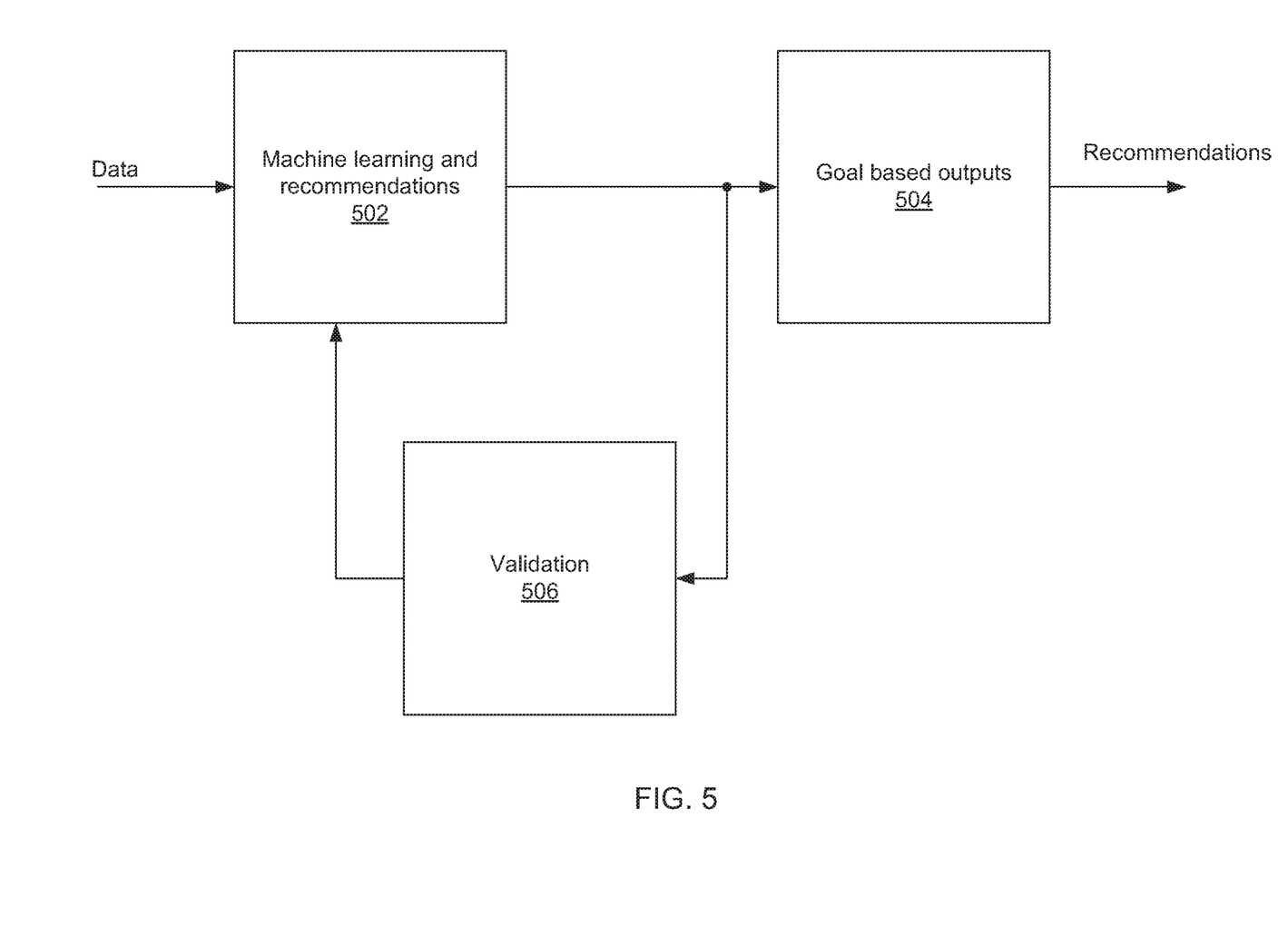
FIG. 5 is a diagram illustrating the use of machine learning in accordance with an embodiment of the present disclosure.

FIG. 5 is a diagram illustrating the use of machine learning in accordance with an embodiment of the present disclosure. Referring to FIG. 5, there is shown a machine learning and recommendations process with feedback. The machine learning process 502 may receive various data from various electronic devices as described previously. Depending on a pre-determined goal that may have been entered by a user, the machine learning process 502 may provide goal based outputs 504. The goal based outputs 504 may then be provided as recommendations to the user. The goal based outputs 504 may also be fed back for validation 506 that a recommendation is useful.

For example, a user with diabetes may configure a profile with a desired goal of reducing and/or controlling the blood glucose level trend. Accordingly, blood glucose level trend of the user in relation to his/her lifestyle data (e.g., activity data), laboratory test results, and food consumption data may be monitored to provide health profile recommendations. One recommendation may be regarding supplemental food products for consumption at specified times based on the relationship between the blood glucose level trend and the user's lifestyle data. Another recommendation may be supplemental activities that the user can perform.

One or more of various types of data such as, for example, lifestyle data, clinical data, health measurement data, environmental data, food consumption data, etc. may be received from one or more electronic devices including, but not limited to, a mobile device 114 (e.g., a cell phone, a tablet, a laptop), a wearable electronic device (e.g., a smart watch 106), a smart appliance 104 (e.g., a smart refrigerator), a smart car 108, one or more sensors 110, a data exchange platform 112, etc.

The lifestyle data may provide an indication of the user's lifestyle patterns, including but not limited to, sleep data, physical activity data (e.g., walking, running), stress data, and social/emotional data such as mood data (e.g., happy, sad, grieving). For example, sleep data, activity data, and mood data may be received from a user's smart watch 106. Also, the user's smart refrigerator 104 may provide data that an orange may have been consumed by the user at 1400$h$ on a Monday after a camera in the user's smart refrigerator 104 captures that the orange has been removed. The smart watch 106 may also ask, for example, the user to verify that the user ate the orange.

Various embodiments may further receive food consumption data at specified times of day. For example, the food consumption data may be a text description provided by the user, such as a name of a restaurant, a type of food (e.g., a vegetable type, a seafood type, a meat type), and a common menu name (e.g., shrimp tacos), or a specific name associated with the food item may be entered. Various embodiments may use location information to identify the restaurant. The food consumption data may also be, for example, an image of the food item or an image of the receipt if the food items are listed. Or the food consumption data may be an image of a bar code of the food package. The image(s) may be captured using, for example, the camera function on an electronic device. The nutrition data for the food items eaten may also be received and/or determined based on the food consumption data. For example, a food item may be identified so that the ingredients are known. Or the characteristics associated with the food item (e.g., calories and nutritional information) may be found in a food database.

Various embodiments may further receive clinical data from physician notes, medical reports, and laboratory test results. In the example of the user who has diabetes, a present system may be able to receive medical reports and laboratory test results related to the user's diabetes condition. Various embodiments may further receive environmental data from any electronic device described (and/or others not described), or an external database. Some environmental data may be, for example, weather reports (e.g., describing pollution, humidity, temperature) that may be received from a weather website database. Other sensors in the smart car 108 or other electronic devices may also provide environmental data.

Context data may also be received in various embodiments. Context data may comprise data regarding, for example, events that may affect the composure of the user. For example, stop-and-go traffic may raise the blood pressure of the user, and thus adversely affect the user's ability to lower his blood pressure. Accordingly, various embodiments may then plan future trips for times when traffic is not so heavy, or route trips to encounter the least amount of traffic given other constraints such as required arrival time, etc. The traffic may also be avoided to a certain extent by suggesting a rest period, shopping for needed items (e.g., groceries), or a meal.

Context data that indicates that a driver is getting drowsy may prompt a suggestion to rest, or play an upbeat song on the car radio. The data prior to the driver getting drowsy may be analyzed to determine what conditions lead to that—the amount of sleep, the type of food eaten and when, the road scenery, etc. This process may also be used for a user that is not driving in order to make that user more productive.

At other times, the user may be at a celebration where the user may eat too much rich food and/or drink more alcoholic drinks than recommended. Accordingly, it can be seen that knowing the context of an occasion may enable preventive warnings to be issued, or at least take those special events into account as being non-regular. Knowing about the special events in advance may allow new recommendations for diet and activities that may alleviate to some extent if possible. Also, subsequent recommendations may be temporarily modified for the abnormal occurrence.

In addition to these rare occasions, if the user has flouted the recommendations, then the recommendations may be changed as needed. The amount of change and the times of change may depend on the various data received regarding the user.

While context data may be used as described above, various embodiments need not be limited to only those scenarios. For example, when driving on a trip, various suggestions may be made to the user regarding nearby restaurants that serve the type of food that the user should eat and enjoys. The suggestions may also include, for example, specific menu items based on the recent past history of meals that the user has had.

Accordingly, various embodiments may provide machine learning and recommendation(s) by monitor the health measurement data of the user based on one or more of the user's lifestyle data, food consumption data, environmental data, context data, clinical data, etc. to provide a context and goal specific health profile recommendation to help the user achieve the desired goal. The health profile recommendation may provide one or more suggestions to adjust a nutrition diet, lifestyle, and fitness activities, and may further provide context and goal specific predictive models to prevent adverse events. As an example, the health profile recommendation may include, for example, supplemental food product(s) and one or more supplemental activities. The profile recommendation may also include habits or activities to reduce or give up. For example, the user may be encouraged to stop smoking and/or reduce consumption of alcohol.

For the user with diabetes, an embodiment may derive nutrition data from the food consumption data based on food consumed at meals (e.g., ice-cream) and observe a blood glucose level trend of the user to provide a correlation or an association between type of food consumption and the corresponding blood glucose level trend in relation to lifestyle data such as sleep data and activity data (e.g., number of steps taken in a day or a period). In this way, an association may be developed between a type of food consumption corresponding to a user's health measurement data and the user's lifestyle data (e.g., sleeping habit, activity, etc.). In another embodiment, a present system may provide a recommendation regarding a supplemental activity that can help the user achieve his/her desired goal.

Various embodiments may also provide validation to determine whether the user has complied with the health profile recommendation based on a comparison between the health profile recommendation and corresponding input data. For example, if a health profile includes a recommendation of an activity for 10 minutes, a corresponding activity input data from, for example, the smart watch 106 indicating that activity may be used to validate that the recommendation has been followed. Accordingly, correlating recommendations with various data may give an indication of how well the user is following the recommendations. The progress toward the desired goal may then be correlated to the recommendations to see the effects of following (or not following) the recommendations.

Another example may be if a health profile recommendation includes consumption of a certain food product, determining whether the user has consumed the food product using data from one of more of the electronic devices. For example, if the recommendation is that the user eats vegetables, then there may be validation of whether the user may have consumed the recommended vegetables by detecting whether those vegetables have been removed from the smart refrigerator.

In various embodiments, the food consumption data and/or lifestyle data, as well as other data that may correspond to the health profile recommendation, may be provided as feedback to the machine-learning and recommendation process. The machine-learning and recommendation process can then use the feedback data to correlate to the monitored health measurement data to improve and fine-tune the health profile recommendation to provide context and goal specific behavior modification. This may allow the user to better progress toward the desired goal.

For example, based on the lifestyle data of a user with diabetes in association with the user's blood glucose level data, the recommendation process may recommend food type A to the user to consume at a specified time. However, if it is observed that the consumed food type A does not cause the blood glucose level to fall sufficiently below a desired threshold level, this information may be fed back to the machine learning process. Accordingly, the machine learning process may consider the food type A with the lifestyle data and provide another recommendation for food type B rather than food type A. In this way, the machine learning process can identify the food products that cause elevated blood glucose and exclude those food products from the recommendation process.

In another example, a user's lifestyle activity data combined with underlying changes in a user's metabolism (e.g., heart rate, progress toward a weight loss goal, etc.) may be used to improve and fine-tune the health profile recommendation. Accordingly, in reaction to various data input, the machine-learning and recommendation process may be able to continuously modify and personalize the machine learning process for each user to increase the likelihood of the user achieving the desired goal.

Figure 6:
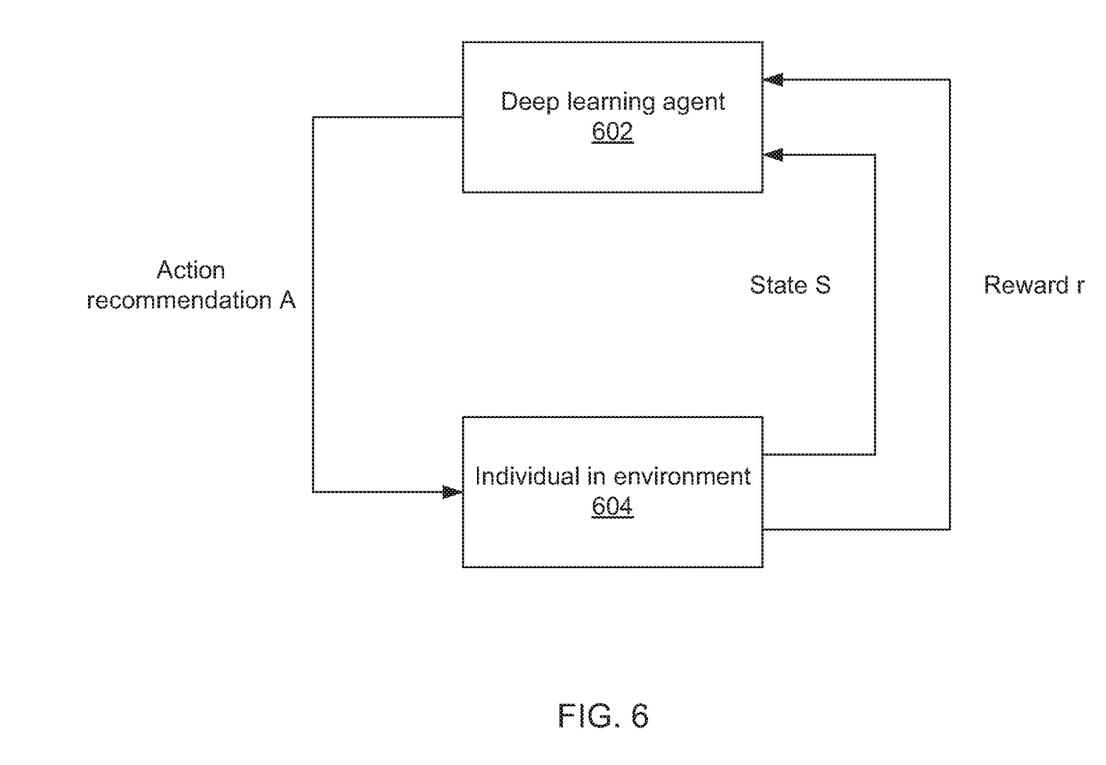
FIG. 6 is a model illustrating the use of deep learning in accordance with an embodiment of the present disclosure.

FIG. 6 is a model illustrating the use of deep learning in accordance with an embodiment of the present disclosure. The model may represent the deep learning agent's representation of a user in the environment. In this model, the State s comprises a person's health indicators including data from sensors, diet and food consumption, contextual information, etc. The Reward $r_t$ is the goal to be minimized or maximized, such as, for example, the user's weight or heart health. The Action a is a recommendation or guidance such as, for example, food recommendation, activity suggestions, mandatory actions like taking medication, etc.

The deep learning agent 602 processes the various data and Rewards from the individual 604 to determine Action recommendation(s). Accordingly, the deep learning agent 602 may be similar to the machine learning process 502. The individual 604 may be the user in the environment who acts on the recommendations from the deep learning agent 602 to achieve a desired goal.

A mapping from the State to Actions may be represented by the Policy it, where the Policy may try to maximize or minimize, as appropriate, a related value function. The value function at each State represents how good the Action(s) are at the given State. Q-value gives an expected total Reward, and a Q-value function shown in Equation 1 gives the expected total Reward from State s and Action a under policy π with discount factor γ:

$$Q^\pi(s,a)=E[r_{t+1}+\gamma r_{t+2}+\gamma^2 r_{t+3}+\ldots|s,a] \quad \text{Equation 1}$$

An optimal value function is the maximum achievable value, and may be expressed by Equation 2:

$$Q^*(s,a)=\max_\pi Q^\pi(s,a)=Q^{\pi^*}(s,a) \quad \text{Equation 2}$$

And the Action to achieve this is given in Equation 3:

$$\pi^*(s)=\mathrm{argmax}_a Q^{\pi^*}(s,a) \quad \text{Equation 3}$$

In various embodiments of the disclosure, a deep reinforcement learning model such as, for example, a deep Q-network (DQN) where a deep neural network represents and learns the model, policy, and value function may be used. Various embodiments may use stochastic gradient descent to optimize the loss function.

Figure 7:
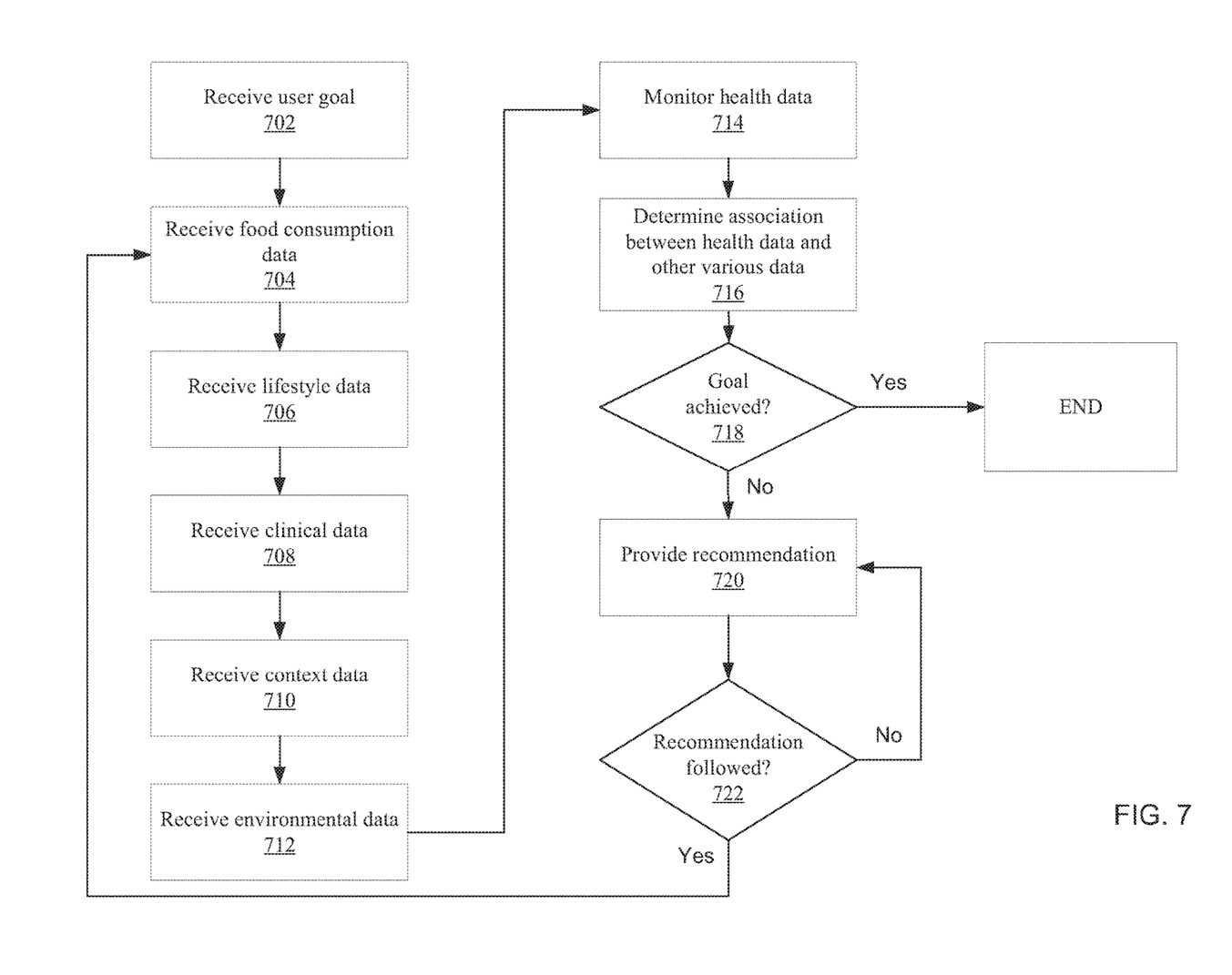
FIG. 7 illustrates an example flow chart for providing machine learning health and behavior insights in accordance with an embodiment of the present disclosure.

FIG. 7 illustrates an example flow chart for providing machine learning health and behavior insights in accordance with an embodiment of the present disclosure. At 702, a desired user goal may be entered by the user via any appropriate input device. If there is not a user health profile available, then various data may also need to be entered about the user. For example, the information needed may be the sex, age, weight, height, type of activity performed by the user (sedentary, physically active, etc.), resting heart rate, blood pressure, etc. Some of the data may be available via various inputs (clinical data, for example). Others may be from answers to questions posed during the initial part of the process.

The goal may be entered using a keyboard, selecting from one or more menus, speaking to a microphone, writing using a finger or a computer input pen, mouse, trackball, etc. A user interface of an application on an electronic device, whether mobile or not, may be used to enter the goal. At 704 through 712, one or more of food consumption data, lifestyle data, clinical data, context data, and environmental data are received. While the data are shown as being received sequentially, various embodiments of the disclosure need not be so limited. The data can be received in any order at any time. Additionally, when data are received via packets, two sequential packets for lifestyle data may be separated by one or more packets for other types of data.

At 714, the user's health measurement data may be received or monitored. In one embodiment, health measurement data may be received from the user's smart watch 106.

A correlation or association may be made between the health measurement data and one or more of the food consumption data, lifestyle data, clinical data, context data, etc. The association may allow the monitored health data to be taken in context. For example, if the user ate recently, then a glucose input data soon after the meal may be ignored.

However, when a user does not have a history of being monitored, a generic user profile may be used. This profile may be generated from aggregated data of various people with similar health/life characteristics as the user. For example, they may be of similar age, height, weight, and ethnic/racial background. They may have similar lifestyle (active, sedentary, etc.) and eating habits (e.g., vegetarian). As more data is gathered about the user over time, the user profile and recommendations will be more personalized for the user.

At 716, an association may be made between the monitored health data and the various received data. At 718, a determination may be made as to whether the user has achieved the desired user goal based on the monitored health measurement data. At 718, if the desired user goal is achieved, for example, by having lost a certain amount of weight, then the process may be finished. At 718, if the desire goal has not been achieved, the health profile recommendation may be modified (e.g., a supplementary food product, a supplemental activity) at 720 so that the user can achieve the desired goal. For a new goal that was entered at 702, the health profile recommendation will be first suggested at 720.

At 722, an embodiment may determine whether the user has followed the health profile recommendation. For example, an embodiment may check whether the user has consumed a supplementary food product using the food consumption data provided by the user and/or whether the food product is detected by one or more of the electronic devices as having been removed, and presumably consumed. In another example, an embodiment may check whether the user has performed a supplemental activity based on activity data tracked by the user's smart watch 106.

If the user has not followed the health profile recommendation, the health profile recommendation or an alternative health profile recommendation may be provided to the user at 720. There may be analysis of specific parts of the recommendation that may not have been followed to provide better recommendations in the next iteration. If the user has followed the health profile recommendation, a present system returns to receive one or more of subsequent food consumption data, lifestyle data, context data, environmental data, and clinical data from the one or more electronic devices. Thus, as the present machine-learning and recommendation process receives more data inputs during an increasing period of time, the more accurate and personalized the machine learning process becomes.

The process described in FIG. 7 is not the only process that can be used by the various embodiments. For example, other types of data may also be used and/or different methodologies may be used. One such variation is described in FIG. 8.

Figure 8:
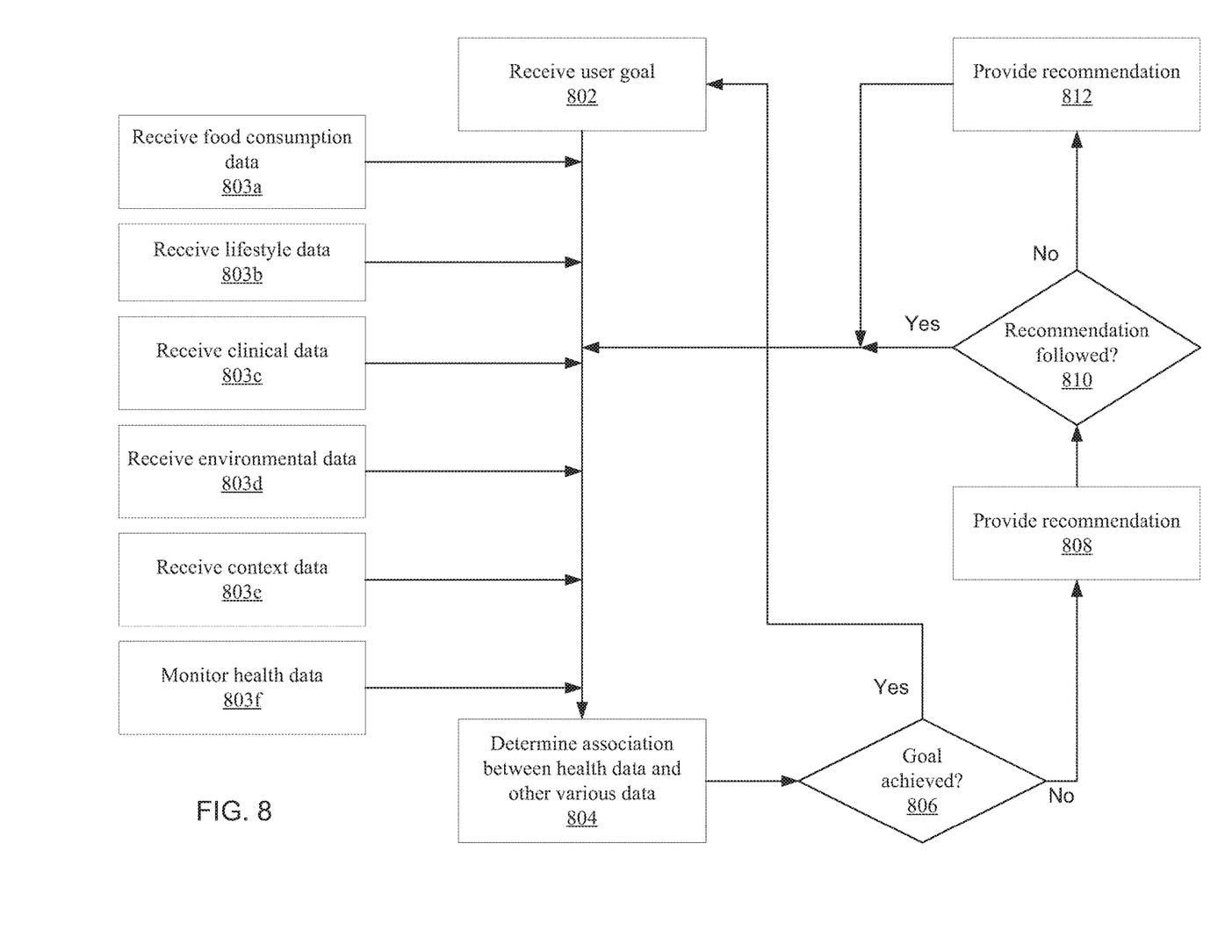
FIG. 8 illustrates another example flow chart for providing machine learning health and behavior insights in accordance with an embodiment of the present disclosure.

FIG. 8 illustrates another example flow chart for providing machine learning health and behavior insights in accordance with an embodiment of the present disclosure. The flowchart FIG. 8 is similar to the flowchart of FIG. 7.

Referring to FIG. 8, a new user may set a user goal at 802. At 804, an association may be made of the user health data received at 803*f* and the various other data received at 803*a*-803*e*. The association may allow the monitored health data to be taken in context. For example, if the user ate recently, then a glucose input data soon after the meal may be ignored.

At 806, if the goal has been met based on the associated results of 804, then an inquiry may be made to the user for another goal. For example, the user may have made a 5 pound weight loss as a first goal, and after achieving that, may make a 10 pound weight loss as the next goal, or make a goal of improving strength, etc.

If the user has not achieved the desired goal, then further recommendations may be made at 808. The recommendation may be the same as the previous recommendation, or the recommendation may have changed due to other received inputs. For example, the user may have eaten too much rich food at a celebratory dinner. Accordingly, depending on the specific goal, the new recommendations may take the unexpected rich food into account. The new recommendation may be temporary or more long term depending on the amount of deviation in the monitored health data due to the rich food, and/or association with the various other received data.

At 810, the user may be monitored to validate whether various parts of the recommendation are being followed. If the recommendation was followed, then the next step is at 804 once again.

However, if a part of the recommendation is not validated, then the next step may be at 812. For example, part of the recommendation may be to take a brisk walk for 30 minutes a day. If there is no input that indicates that the user has taken this walk, depending on the circumstances including the length of time that the recommendation was not followed, and how much of the recommendation was not followed, a new recommendation may be provided at 812. The next step is then at 804.

As can be seen by the slight variation between the process of FIG. 7 and the process of FIG. 8, there may be many processes that can be used with various embodiments of the disclosure.

Various embodiments of the disclosure may break up a goal into different phases that may be based on a knowledge database or an aggregation of data for people with similar profile and their success rates for different methods of achieving the goal. For example, when a user indicates that he has diabetes, the first phase may be to have the user lose weight and learn blood glucose level response, then the second phase may be to provide recommendations that focus on diabetes.

Various embodiments of the disclosure may be written as computer programs and may be implemented in general-use digital computers that execute the programs using a non-transitory computer-readable recording medium.

Non-transitory computer-readable recording medium may include, for example, magnetic storage media (e.g., ROM, floppy disks, hard disks, etc.), optical recording media (e.g., CD-ROMs, or DVDs), etc.

While various embodiments of the disclosure have been described with reference to the figures, it will be understood by those of ordinary skill in the art that various changes in form and details may be made therein without departing from the spirit and scope of the disclosure as defined by the following claims. Accordingly, the above embodiments and all aspects thereof are examples only and are not limiting.

What is claimed:

1. A method for monitoring health of a user, the method comprising:
receiving, with a device worn by the user, user-related data from at least one electronic device not worn by the user, wherein a strap of the device includes a sensor;
processing signals of the sensor with a processor in the strap;
monitoring health-related data of the user via the processed signals of the device worn by the user, wherein the device worn by the user places the sensor in close proximity to the user, and wherein monitoring the health-related data of the user comprises generating, via the sensor of the device worn by the user, the health-related data during monitoring periods;
receiving, with the device worn by the user, a goal from the user;
generating, with a machine-learning and recommendation process, goal based outputs for furthering the goal;
providing, based on the generated goal based outputs, at least one recommendation to the user via the device worn by the user to perform an action directed toward furthering the goal;
providing the generated health-related data received from the sensor of the device after performance of the action as feedback to the machine-learning and recommendation process; and
modifying the machine-learning and recommendation process, based on and in response to the generated health-related data that was provided as feedback, to improve the generated goal based outputs.

2. The method of claim 1, wherein providing the at least one recommendation comprises using a deep Q-network to determine the at least one recommendation.

3. The method of claim 1, wherein providing the at least one recommendation comprises using deep learning to determine the at least one recommendation.

4. The method of claim 1, wherein the goal is to control a blood glucose level of the user.

5. The method of claim 1, comprising:
monitoring the user to determine whether the user is following the at least one recommendation, wherein monitoring the user to determine whether the user is following the at least one recommendation comprises:
presenting, via the device worn by the user, a request for confirmation that the action was performed; and
receiving, via the device worn by the user, a response to the request for confirmation.

6. The method of claim 1, wherein the user-related data comprises food consumption data.

7. The method of claim 1, comprising:
transmitting, via a communication interface of the device worn by the user, the user-related data and the health-related data to a cloud-based electronic device; and
receiving, via the communication interface of the device worn by the user, the at least one recommendation.

8. The method of claim 1, wherein providing the at least one recommendation to the user comprises presenting the at least one recommendation to the user via a display of the device worn by the user.

9. The method of claim 1, comprising prolonging life of a battery of the device worn by the user by periodically alternating between the monitoring periods in which the sensor continuously generates the health-related data and non-monitoring periods in which the sensor does not continuously generate the health-related data.

10. The method of claim 1, comprising strapping the device around a body part of the user such that the strap places the sensor in contact with the user.

11. The method of claim 1, comprising controlling a display of the device worn by the user with another processor of the device worn by the user.

12. A method for monitoring health of a user, the method comprising:
  monitoring health-related data of the user via a sensor in a strap of a smartwatch that is strapped around a wrist of the user, wherein monitoring comprises processing signals of the sensor with a processor in the strap;
  receiving, with the smart watch strapped around the wrist of the user, user-related data from at least one electronic device;
  generating, with a machine-learning and recommendation process based on the user-related data and the health-related data, goal based outputs for a goal of the user;
  generating, based on the generated goal based outputs, at least one recommendation;
  presenting the at least one recommendation via a display of the smartwatch strapped around the wrist of the user;
  feeding back the goal based outputs to the machine-learning and recommendation process;
  modifying the machine-learning and recommendation process based on the fed back goal based outputs to improve the generated goal based outputs; and
  prolonging life of a battery of the smartwatch by periodically alternating between monitoring periods in which the sensor generates the health-related data and non-monitoring periods in which the sensor does not generate the health-related data.

13. The method of claim 12, comprising:
  receiving, via a microphone of the smartwatch, a goal from the user,
  wherein presenting the at least one recommendation instructs the user to perform an action directed toward furthering the goal.

14. The method of claim 13, comprising:
  presenting, via the smartwatch, a request for confirmation that the action was performed; and
  receiving, via the smartwatch, a response to the request for confirmation.

15. The method of claim 12, wherein generating the at least one recommendation comprises using deep learning to map a state S to an action a per a policy $\pi$, wherein the policy $\pi$ maximizes or minimizes a related value function.

16. The method of claim 3, wherein using the deep learning comprises mapping a state S to an action a per a policy $\pi$, wherein the policy $\pi$ maximizes or minimizes a related value function.

* * * * *